(12) United States Patent
Shroff et al.

(10) Patent No.: US 8,461,386 B2
(45) Date of Patent: Jun. 11, 2013

(54) HYDROGENATION OF IMINES

(75) Inventors: Jaidev Rajnikant Shroff, Mumbai (IN); Vikram Rajnikant Shroff, Mumbai (IN); Birja Shanker, Mumbai (IN)

(73) Assignee: United Phosphorus Limited, Maharashtra (IN)

( * ) Notice: Subject to any disclaimer, the term of this patent is extended or adjusted under 35 U.S.C. 154(b) by 266 days.

(21) Appl. No.: 12/935,166

(22) PCT Filed: Apr. 16, 2009

(86) PCT No.: PCT/IN2009/000237
§ 371 (c)(1),
(2), (4) Date: Nov. 18, 2010

(87) PCT Pub. No.: WO2009/136409
PCT Pub. Date: Nov. 12, 2009

(65) Prior Publication Data
US 2011/0054217 A1     Mar. 3, 2011

(30) Foreign Application Priority Data
Apr. 17, 2008 (IN) ............... 877/MUM/2008

(51) Int. Cl.
*C07C 209/70* (2006.01)
*C07C 233/18* (2006.01)

(52) U.S. Cl.
USPC ................ 564/209; 564/415; 564/443

(58) Field of Classification Search
USPC ................................ 564/209, 415, 443
See application file for complete search history.

(56) References Cited

U.S. PATENT DOCUMENTS

| 6,166,257 A | 12/2000 | Mathey et al. |
| 6,822,118 B1 * | 11/2004 | Jalett et al. .................. 564/211 |
| 2006/0089469 A1 | 4/2006 | Komarov et al. |
| 2007/0213540 A1 | 9/2007 | Perea et al. |

OTHER PUBLICATIONS

Schmitt et al, J.of Chromatography A, 792, 1997, p. 419-429.*
Blaser, "The Chiral Switch of (S)-Metolachlor: A Personal Acount of an Industrial Odyssey in Asymmetric Catalysis" Advanced Synthesis and Catalysis, vol. 344, No. 1, 2002, pp. 17-31.
Colacort, "A Concise Update on the Applications of Chiral Ferrocenyl Phosphines in Homogeneous Catalysis Leading to Organic Synthesis", Chem. Rev. vol. 103, 2003, pp. 3101-3118.
Komarov, et al., "A new hydroxydiphosphine as a ligand for Rh(I)-catalyzed enantioselective hydrogenation", Tetrahedron: Asymmetry, vol. 13, No. 15, 2002, pp. 1615-1620.

* cited by examiner

*Primary Examiner* — Shailendra Kumar
(74) *Attorney, Agent, or Firm* — Hamre, Schumann, Mueller & Larson, P.C.

(57) ABSTRACT

The present invention relates to a process for the asymmetric hydrogenation of imines with hydrogen under elevated pressure in the presence of a catalyst system. In particular the present invention relates to the use of the said catalytic system for the enantioselective hydrogenation of prochiral ketimines to asymmetric amines leading to the formation of herbicides.

19 Claims, No Drawings

HYDROGENATION OF IMINES

This application is a 371 of PCT/IN2009/000237, filed Apr. 16, 2009.

FIELD OF THE INVENTION

The present invention relates to a process for the asymmetric hydrogenation of imines with hydrogen under elevated pressure in the presence of a catalyst system. The invention particularly relates to the use of the said catalytic system for the enantioselective hydrogenation of prochiral ketimines to asymmetric amines leading to the formation of herbicides.

BACKGROUND AND PRIOR ART

Catalytic hydrogenation of imine has been known for a relatively long time. In organic synthesis, catalytic hydrogenation processes using either homogeneous catalysts or heterogeneous catalysts have played an important role. Heterogeneous catalysts are insoluble; thus they can be readily separated from the reaction mixture and generally, offer the potential for ready re-use whereas homogeneous catalysts are soluble and so difficulties can be encountered in separating the homogeneous catalyst, both the metal and the accompanying ligands, from the product. This not only presents problems with the purity of the product, but also makes the re-use of the homogeneous catalyst problematic. These catalysts are known to exhibit the advantages of catalyzing hydrogenation reactions in the synthesis routes for the preparation of various herbicides with remarkable chemical specificity under relatively mild conditions. Accordingly, there is an increased emphasis on the use of such catalysts in the preparation of herbicides on a commercial scale.

One such catalyst system which has demonstrated good industrial potential for the hydrogenation of imines is the homogeneous iridium—xyliphos catalyst system, which has found extensive applicability for the preparation of various herbicides especially in the preparation of (S)-2-chloro-N-(2-ethyl-6-methylphenyl)-N-(2-methoxy-1-methylethyl)acetamide [Hans-Ulrich Blaser, *Advanced Synthesis and Catalysis*, 2002, 344,17-31].

These homogeneous catalysis processes have proved valuable. It has been observed in the case of relatively large batches or on an industrial scale, that the catalysts frequently tend to become deactivated to a greater or lesser extent depending on the catalyst precursor, the substrate and the ligands that are used. In many cases, especially at elevated temperatures it is not possible to achieve complete conversion; therefore, the catalyst productivity is too low from the point of view of economic viability.

Advanced synthesis and catalysis, vol. 34, pp.17-31 (2000), discusses hydrogenation of imines using Ir-xyliphos ligand, acetic acid as a solvent and an iodide as an additive. This publication discloses that in the presence of acetic acid and iodide additive, the catalyst activity of an Iridium-xyliphos catalyst system increased by a factor of 10 and the ee increased by 5-6%. However, the simultaneous presence of acetic acid and an iodide additive is required to achieve an appreciable conversion as the catalyst system per se. In the absence of added acetic acid and iodide additive, the catalyst shows negligble turn-over-frequency and enantiomeric selectivity. The use of acetic acid requires specialized equipment constructed of a corrosion resistant material, which increases the costs. Moreover, acetic acid leads to the formation of hydrogen iodide and other metal salts, which further makes the reaction workup complicated. Thus, it is desirable to arrive at a process for asymmetric hydrogenation of an imine involving a catalyst system that avoids the presence of acetic acid and still achieve an appreciable turn-over-frequency and enantiomeric selectivity.

The chemistry of synthesis of chiral fine chemicals, pharmaceuticals and agrochemicals has become increasingly more complicated often requiring multi-step reactions involving complicated catalyst systems, such as, e.g., expensive organometallic catalyst systems. Consequently, there has been increased emphasis on the development of new catalyst systems which have high activity and selectivity and which maintain their catalytic activity for a relatively extended period of time under desired reaction conditions.

Hitherto, there have been numerous attempts in the art towards an enantiomeric selective catalyst system for effecting stoichiometric efficient asymmetric hydrogenation of imines.

U.S. Pat. No. 6,822,118 describes a process for the hydrogenation of imines with hydrogen under elevated pressure in the presence of homogeneous iridium catalysts with appropriate ligand and with or without an inert solvent, wherein the reaction mixture contains an ammonium or metal chloride, bromide or iodide and additionally an acid. The catalysts in these homogeneous processes cannot be recovered or can be recovered only with expensive separation methods, which is always associated with undesirable losses. Thus, there remains a need in the art for a process for asymmetric hydrogenation of imines involving an improved catalyst system that overcomes the disadvantages associated with these hitherto known catalysts.

Chem. Reviews, 2003, 103, 3101-3118 discloses the ferrocenyl phosphine, xyliphos and josiphos ligands for hydrogenation of imines. This literature discusses the use of iodide and acid as additives for hydrogenation of imines. The disclosed process again requires the simultaneous presence of acetic acid and an iodide additive to achieve an appreciable turn-over-frequency and enantiomeric selectivity. However, as discussed above, the simultaneous presence of acetic acid and an iodide additive is undesirable.

US 2006/089469, whose contents are incorporated herein by reference in entirety, discloses asymmetrical, chiral hydroxyl diphosphines and their use as catalysts for enantioselective synthesis. The described organophosphorus compounds are combined with metal complex precursors in order to provide a suitable catalyst system. Paragraph [0025] discloses particularly preferred catalyst systems according to the invention disclosed comprising Ru and Rh complexes containing the described ligands.

This patent teaches the preparation of a ligand [(1R, 2R, 3S)-1,2-Dimethyl-2,3-bis(diphenylphosphinomethyl)cyclopentyl] methanol, while example 6 discloses the preparation of its Rh complex. Example 7 discloses the use of the rhodium complex prepared in accordance with example 6 for various hydrogenation reactions. This exemplified catalyst system is not disclosed to have been preferred for the asymmetric hydrogenation of an imine. Moreover, all the exemplified reactions were carried out at room temperature under a hydrogen pressure of 1 bar, which is contrary to the finding of the present invention.

It has further been observed on an industrial scale that the catalyst systems frequently tend to become deactivated depending on the catalyst precursor, the substrate and the ligands. It has further been found that not all catalyst systems that are known in the art enable a complete conversion of the starting materials into the target product with a high enantiomeric selectivity.

S-Metolachlor is one of the most important grass herbicides for use on soyabean, maize and other various crops. The racemic form of this known herbicide contains two chiral elements, a chiral axis and a stereogenic center leading to four stereo-isomers. It later came to be known that about 95% of the herbicidal activity of metolachlor resided in the two 1-S diastereomers. This meant that the same biological effect could be produced at about 65% of the use rate of the racemic product. However, a commercially feasible process for the enantioselective manufacture of S-Metolachlor has been compared to moving in a complicated labyrinth. The search for a catalyst for the enantioselective manufacture of S-Metolachlor is likened to a walk in a labyrinth that covers the "TON-EE" space i.e. finding a catalyst with a sufficient stereospecificity (greater than 74% enantiomeric excess) as well as productivity (at least 99% conversion efficiency). Thus, finding an efficient and enantioselective catalyst for the preparation of S-Metolachlor has been a long felt and challenging need in the art of herbicide synthesis.

Thus, there is a continuous need in the art for a process that enables an enantioselective hydrogenation of imines with a high conversion as well as a high enantiomeric excess of the target product wherein the catalyst system is cost effective.

OBJECTS OF THE INVENTION

Accordingly, it is an object of the present invention to provide a process for the asymmetric hydrogenation of imines.

It is yet another object of the present invention to provide a process for the asymmetric hydrogenation of imines in presence of catalyst system.

It is yet another object of the present invention to provide a process for the asymmetric hydrogenation of imines wherein the employed catalyst system comprises a ligand and a metal or a salt thereof.

Yet another object of the present invention is to provide a process for the asymmetric hydrogenation of imines having high conversion efficiency and high enantiomeric excess.

Yet another object of the present invention is to provide a process for the asymmetric hydrogenation of imines to an amine, which is useful for the preparation of S-Metolachlor.

SUMMARY OF THE INVENTION

A process for asymmetric hydrogenation of an imine having formula 1:

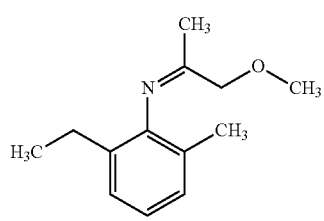

to obtain an amine having formula 2:

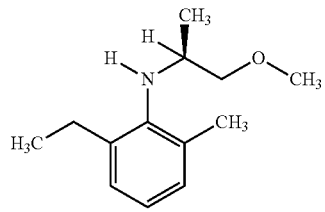

said process comprising contacting said imine having the above formula 1 with hydrogen under elevated pressure in a predetermined organic solvent in the presence of a catalyst system;
said catalyst system comprising a ligand complexed to a metal selected from iridium and rhodium or a salt thereof; wherein said ligand is selected from a group comprising
(a) [(1R,2R,3S)-1,2-dimethyl-2,3-bis(diphenylphosphinomethyl)-cyclopentyl]methanol;
(b) (1S,4S, 11R)-1,11-bis-[(diphenylphosphanyl)-methyl]-11-methyl-1,2,3,4-tetrahydro-1,4-methanophenazin;
(c) (R)-3-Di-(3,5-dimethylphenyl)phosphino-2-(4-diphenylphosphino-2,5-dimethylthienyl-3)-1,7,7-trimethylbicyclo-[2.2.1]-hept-2-ene;
(d) (S)-2-[(o-diphenylphosphino)-phenyl]-1-diphenylphosphino-ferrocene;
(e) (S)-1-(Diphenylphosphino)-2-(S)-(o-diphenylphosphino-α-methoxybenzyl)ferrocene;
(f) (+)-(S)-N,N-Dimethyl-1-[(R)-1',2-bis-(Diphenylphosphino)-ferrocenyl]-ethylamine; and
(g) [(S)-1-[(R)-2-diphenylphosphino)ferrocenyl]-ethyl-di(cyclohexyl)-phosphine.

In another aspect, the present invention provides an improved process for asymmetric hydrogenation of an imine having formula 1:

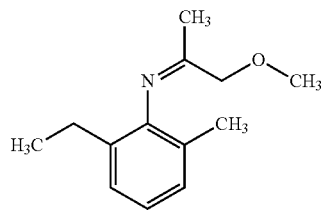

to obtain an amine having formula 2:

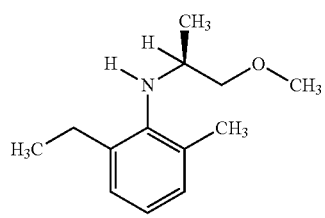

said process comprising contacting said imine having the above formula 1 with hydrogen under an elevated pressure of 80 bar at a temperature of about 50° C. in toluene in the presence of a catalyst system comprising a ligand having a formula [(1R,2R,3S)-1,2-dimethyl-2,3-bis(diphenyl phosphine methyl)-cyclopentyl]methanol complexed to iridium metal or a salt thereof.

DETAILED DESCRIPTION OF THE INVENTION

Therefore, in an aspect, the present invention provides an enantiomeric selective process for the hydrogenation of imine with hydrogen under elevated pressure in presence of a catalyst system comprising a pre-defined bidentate diphosphine ligand complexed to a metal in presence of a predetermined inert solvent.

The imine preferably includes a compound having the formula 1

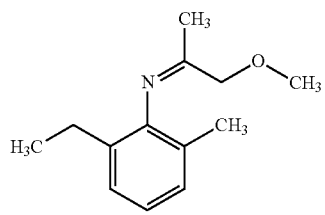

1 which is asymmetrically hydrogenated to an amine having the following formula 2:

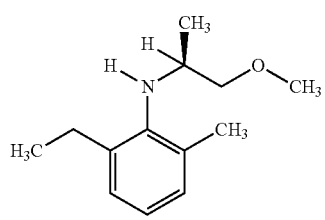

2

Hitherto, the catalyst systems of the present invention have not been used for carrying out the hydrogenation of an imine, particularly an imine having the formula 1 described above and more so at an elevated hydrogen pressure preferred according to the present invention. It has been surprisingly found that reacting an imine having the formula 1 with hydrogen under elevated pressure in an inert solvent in the presence of a catalyst system comprising a predetermined ligand complexed to a metal selected from iridium and rhodium resulted into a high conversion efficiency and high enhanced enantiomeric selectivity in the formation of the resultant amine of formula 2. The substrate to catalyst ratio during said hydrogenation reaction of the present invention varied from about 200 to about 500000.

The predetermined ligand is selected from a group comprising:
(a) [(1R,2R,3S)-1,2-dimethyl-2,3-bis(diphenylphosphinomethyl)-cyclopentyl]methanol;
(b) (1S,4S,11R)-1,11-bis-[(diphenylphosphanyl)-methyl]-11-methyl-1,2,3,4-tetrahydro-1,4-methanophenazin;
(c) (R)-3-Di-(3,5-dimethylphenyl)phosphino-2-(4-diphenylphosphino-2,5-dimethylthienyl-3)-1,7,7-trimethyl-bicyclo-[2.2.1]-hept-2-ene;
(d) (S)-2-[(o-diphenylphosphino)-phenyl]-1-diphenylphosphino-ferrocene;
(e) (S)-1-(Diphenylphosphino)-2-(S)-(o-diphenylphosphino-α-methoxybenzyl)ferrocene;
(+)-(S)-N,N-Dimethyl-1-[(R)-1',2-bis-(Diphenylphosphino)-ferrocenyl]-ethylamine; and
(g) [(S)-1-[(R)-2-diphenylphosphino)ferrocenyl]-ethyl-di(cyclohexyl)-phosphine.

The compound of formula 2 described above is thereafter reacted with chloroacetyl chloride in the presence of a base in a non-polar solvent at pre-defined temperatures to obtain a compound of formula 3. This reaction step is preferably carried out at a temperature of from about 0° C.-5° C.

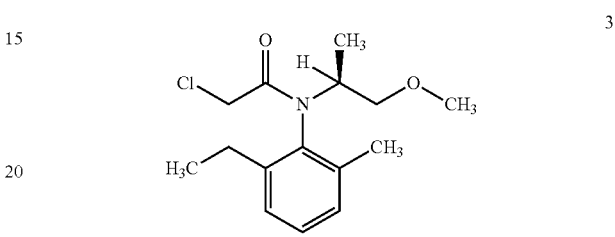

3

The compound of formula 3 described above is commercially marketed herbicide known as S-Metolachlor.

The compound of formula 1 may be prepared by reacting a compound of the formula 4 (2-ethyl-6-methyl aniline) with a corresponding ketone. For example, the compound having the following formula 4:

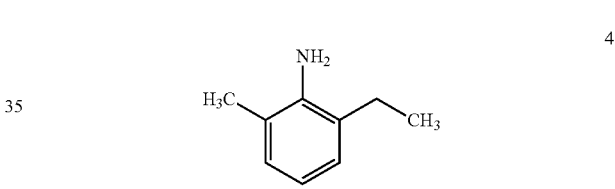

4 is reacted with a ketone having the formula $CH_3OCH_2C(O)CH_3$ (methoxyacetone) to obtain a compound of formula 1. This reaction is conventionally known in the art and may be carried out using the known methods per se.

Although the process hereinabove has been described with reference to the specific imine compound of formula 1, it would readily occur to a person skilled in the art that it could be as conveniently carried out on an aryl imine as depicted hereunder.

The schematic representation of the chemical reaction occurring during the hydrogenation reaction of an aryl imine according to this aspect of the present invention is as hereunder:

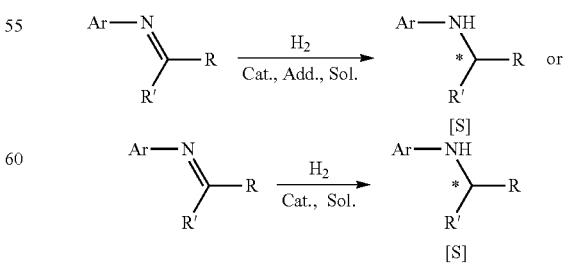

wherein R is $C_1$-$C_4$ alkyl, preferably methyl; R' is $C_1$-$C_4$ alkoxy alkyl, preferably $C_1$-$C_4$ alkoxymethyl or $C_1$-$C_4$ alkoxyethyl, preferably methoxymethyl and Ar is phenyl substituted by one or more $C_1$-$C_4$ alkyl.

The amine obtained from hydrogenation of imine can be converted in accordance with methods that are customary per se with chloroacetyl chloride into the desired herbicides of the chloroacetanilide type.

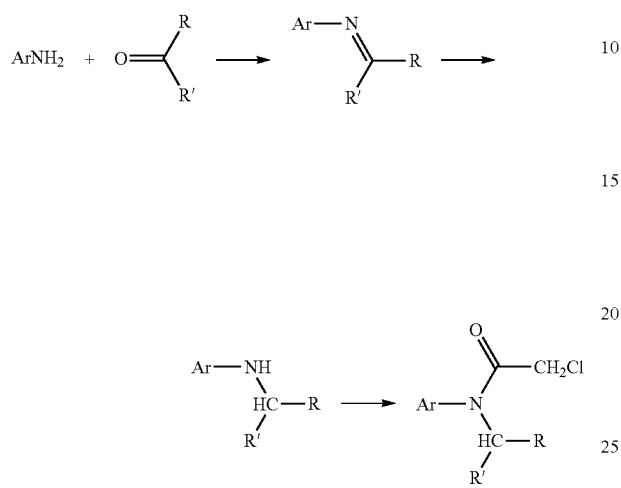

In an embodiment of the present aspect, said metal is preferably selected from Iridium, Rhodium or a salt thereof.

The structures of the ligands that are preferred according to the present invention are shown below:

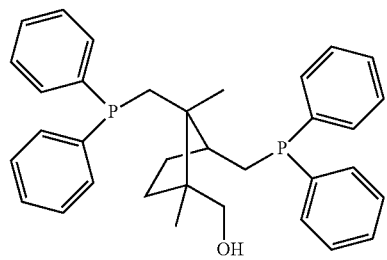 [SMILES: CC1(CO)CCC(CP(c2ccccc2)c2ccccc2)C1(C)CP(c1ccccc1)c1ccccc1]

(I) [(1R,2R,3S)-1,2-dimethyl-2,3-bis(diphenylphosphinomethyl)-cyclopentyl]methanol

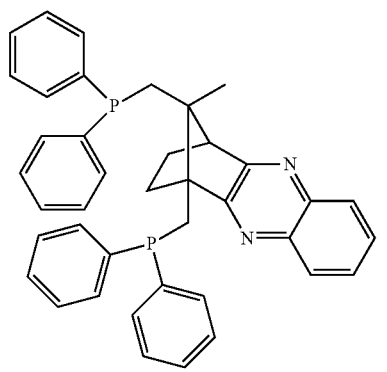

II (II) (1S,4S, 11R)-1,11-bis-[(diphenylphosphanyl)-methyl]-11-methyl-1,2,3,4-tetrahydro-1,4-methanophenazin

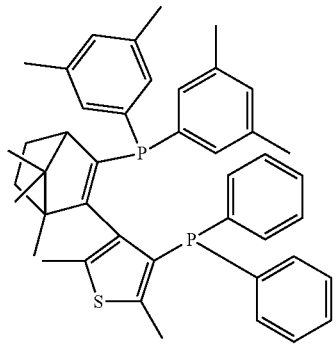

(III) (R)-3-Di-(3,5-dimethylphenyl)phosphino-2-(4-diphenylphosphino-2,5-dimethylthienyl-3)-1,7,7-trimethylbicyclo-[2.2.1]-hept-2-ene

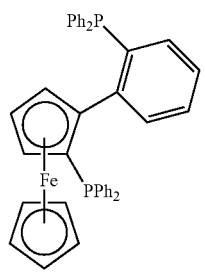

(IV) (S)-2-[(o-diphenylphosphino)-phenyl]-1-diphenylphosphino-ferrocene

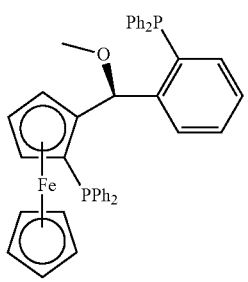

(V) (S)-1-(Diphenylphosphino)-2-(S)-(o-diphenylphosphino-α-methoxybenzyl)ferrocene

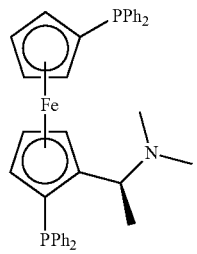

VI (VI) (+)-(S)-N,N-Dimethyl-1-[(R)-1',2-bis-(Diphenylphosphino)-ferrocenyl]-ethylamine

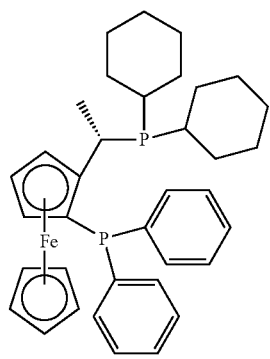

VII (VII) [(S)-1-[(R)-2-diphenylphosphino) ferrocenyl]-ethyl-di(cyclohexyl)-phosphine In an embodiment of the present aspect, said predetermined solvent is an inert organic solvent preferably selected from the group comprising toluene, 1,4-dioxane, methanol, tetrahydrofuran and dichloromethane. The word "inert" as herein in the context of an organic solvent denotes a solvent that does not itself participate in the reaction and is not intended to limit the scope of the invention in any manner.

The process of the present invention further may optionally comprise the addition of a predetermined additive. In a preferred embodiment of the present aspect, said additive is preferably selected from a group comprising diadamantyl butyl phosphonium hydroiodide (A), Diadamantyl benzyl phosphonium hydrobromide (B), Triphenyl phosphonium diiodide (C), Isopropyl triphenylphosphonium iodide (D), Triphenyl phosphonium dibromide (E), Methyl triphenyl phosphonium bromide (F), Tetrabutyl Ammonium Iodide (G), Copper(II) Triflate (H), Yetribium(II) Triflate (I) and Triphenyl phosphonium dichloride (J).

The process of the present invention is carried out at elevated pressure. The term elevated pressure as used herein means pressure ranging from about 5 bar to about 150 bar.

In a preferred embodiment, the process of the present invention is preferably carried out at a temperature of about 50° C. and at a hydrogen pressure of about 80 bar. In this preferred embodiment, the catalyst system comprises a ligand having formula [(1R,2R,3S)-1,2-dimethyl-2,3-bis(diphenylphosphinomethyl)-cyclopentyl]methanol complexed to iridium metal or salts thereof. The process of the present embodiment is preferably carried out in toluene in the presence of an additive having the formula triphenyl phosphonium dibromide.

It has been further surprisingly found according to the present embodiment that even at a high substrate to catalyst ratio of up to about 500000, the resulting amine was found to have undergone at least 99% conversion at ≧76% enantiomeric excess.

Thus, in a preferred embodiment, it was observed that when the process of present invention was carried out using ligand, [(1R,2R,3S)-1,2-dimethyl-2,3-bis(diphenyl phosphinomethyl)cyclopentyl]methanol complexed with a Iridium at a substrate to catalyst ratio of up to about 500 000 in the presence of Triphenyl phosphonium dibromide as a preferred additive in toluene as a preferred solvent, the resulting product was found to have undergone 100% conversion at 76% enantiomeric excess.

It was surprisingly found that the process of the present invention afforded ≧99% conversion and ≧76% enantiomeric excess even in absence of an additive or an acid which is generally used for hydrogenation of imine for achieving higher conversion and higher enantiomeric excess. The ligands according to the present invention thus avoid the need for a simultaneous presence of acetic acid and an iodide additive, which was required in the conventionally known art in order to achieve an appreciable conversion thereby avoiding the need for a specialized equipment constructed of a corrosion resistant material without compromising the turn-over-frequency and enantiomeric selectivity.

Thus, in another aspect, the present invention provides an improved process for asymmetric hydrogenation of an imine having formula 1:

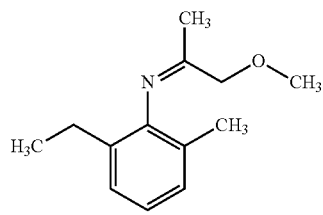

1 to obtain an amine having formula 2:

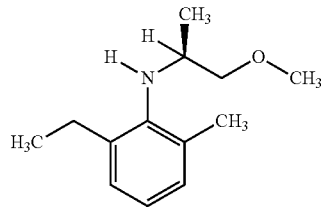

2 said process comprising contacting said imine having the above formula 1 with hydrogen under an elevated pressure of 80 bar at a temperature of about 50° C. in toluene in the presence of a catalyst system comprising a ligand having a formula [(1R,2R,3S)-1,2-dimethyl-2,3-bis(diphenyl phosphine methyl)-cyclopentyl]methanol complexed to iridium metal or a salt thereof.

In an embodiment of this aspect, the process is preferably carried out in the presence of a predetermined additive, which is triphenyl phosphonium dibromide (E).

The invention shall now be described with reference to the following specific examples. It should be noted that the example(s) appended below illustrate rather than limit the invention, and that those skilled in the art will be able to design many alternative embodiments without departing from the scope of the appended claims. Other than in the operating examples provided hereunder, or where otherwise indicated, all numbers expressing quantities of ingredients or reaction conditions are to be understood as being modified in all instances by the term "about".

Example 1 i) Hydrogenation of 2-ethyl-N-(1-methoxypropan-2-ylidene)-6-methylaniline using ligand [(1R,2R,3S)-1,2-dimethyl-2,3-bis(diphenyl phosphinomethyl)cyclopentyl)methanol (1) in presence of different additives.

0.001 mmol of ligand, [(1R,2R,3S)-1,2-dimethyl-2,3-bis(diphenyl phosphinomethyl)cyclopentyl]methanol, (I), 0.0005 mmol of [Ir(COD)Cl]$_2$ and 0.004 mmol of the corresponding additive were mixed together under argon in 0.1 ml dichloromethane and the mixture was stirred at room temperature for 20 min. Meanwhile 0.1-5 mmol solution of the substrate in the corresponding solvent was introduced to the autoclave. The catalyst solution was then introduced to the autoclave and the autoclave was purged with hydrogen at an elevated pressure. The reaction mixture was warmed under in oil bath to the desired elevated temperature. After cooling and release of pressure, a sample of the reaction mixture was withdrawn from the autoclave. The solvent was evaporated and residue was dissolved in 200 μl isopropanol and 1 ml n-hexane and filtered through a short path of silica gel column. The filtrate was analyzed by ii) Hydrogenation of 2-ethyl-N-(1-methoxypropan-2-ylidene)-6-methylaniline using Ligand Xyliphos in Presence of Different Additives The experimental procedure of Example 1 (i) above was followed for a ligand {(R)-1-[(S)-2-diphenylphosphino)ferrocenyl]}ethyl-di(3,5-dimethyl)phosphine (xyliphos). The ligand xyliphos is one of the well known ligands which has been used for hydrogenation of imines.

The results for the final product for conversion (%) & ee (%) using different additives and different solvents in presence of ligand-xyliphos and ligands of present invention are tabulated in the accompanying Table 1.

TABLE 1

|  | Ligand: I Acid: none | | | Ligand: xyliphos Acid: acetic acid | | |
|---|---|---|---|---|---|---|
|  | Conversion (%) | ee (%) | Abs. conf. | Conversion (%) | ee (%) | Abs. conf. |
| Additive: D, S/C ratio: 200 solvent: toluene | 100 | 80 | S | 100 | 80 | S |
| Additive: B, S/C ratio: 200 solvent: toluene | 100 | 80 | S | 100 | 76 | S |

The process of the present invention thus eliminates the need for the presence of acetic acid, which requires special handling equipment due to its corrosive nature.

Example 2

Hydrogenation of 2-ethyl-N-(1-methoxypropan-2-ylidene)-6-methylaniline using different ligands.

The experimental procedure of Example I above was followed for the different ligands of present invention. The results for the final product for conversion (%) and ee (%) using different additives and different solvents are tabulated in the accompanying Table 2 wherein ligands and additives are as described before.

TABLE 2

| Sr. No. | Ligand | Solvent | Additive | Conversion (%) | ee (%) | Abs. conf. |
|---|---|---|---|---|---|---|
| 1. | I | Toluene | B | 100 | 80 | S |
| 2. | I | 1,4-dioxane | B | 99 | 77 | S |
| 3. | III | 1,4-dioxane | H | 100 | 76 | S |
| 4. | VI | 1,4-dioxane | A | 100 | 76 | S |
| 5. | VI | 1,4-dioxane | H | 100 | 76 | S |

The results in Table 2 substantiate that the process of the present invention provides high conversion efficiency for the hydrogenation of imines, even in absence of any acid, such that the process enables at least 99% to 100% conversion of the starting material to the target product having >76% enantiomeric excess of the target product.

Example 3

Hydrogenation of 2-ethyl-N-(1-methoxypropan-2-ylidene)-6-methylaniline using ligand (S)-2-[(o-diphenylphosphino)-phenyl]-1-diphenylphosphino-ferrocene (IV)

0.001 mmol of ligand (IV), 0.0005 mmol of [Ir(COD)Cl]$_2$ and 0.004 mmol of additive A were mixed together under argon in 0.1 ml dichloromethane and the mixture was stirred at room temperature for 20 min. Meanwhile 0.1 mmol solution of 2-ethyl-N-(1-methoxypropan-2-ylidene)-6-methylaniline in dichloromethane was introduced to autoclave. Eventually 0.12 ml of acetic acid was added in the autoclave and the autoclave was purged with hydrogen and pressurized to 50 bar. The reaction mixture was warmed under stirring in an oil bath to 50° C. and reaction continued for 18 hr. Reaction mixture was cooled down and after pressure had been released, the final product of reaction mixture was withdrawn from autoclave, solvent was evaporated and the residue was dissolved in 200 μl isopropanol and 1 ml hexane and the whole was filtered through a short path of silica gel. The filtrate was analyzed by HPLC. The conversion of imine to amine was 99% comprising 88% of (S)-2-ethyl-N-(1-methoxypropan-2-yl)-6-methylaniline (ee 76%)

Example 4

Hydrogenation of 2-ethyl-N-(1-methoxypropan-2-ylidene)-6-methylaniline using Different Ligands The experimental procedure of Example 1 above was followed for the different ligands of present invention, wherein substrate to catalyst ratio is 3000. The results for the final product for conversion (%) and ee (%) using different additives and different solvents are tabulated in the accompanying Table 3 wherein ligands and additives are as described before.

TABLE 3

| Sr. No. | Ligand | Solvent | Additive | Conversion (%) | ee (%) | Abs. conf. |
|---|---|---|---|---|---|---|
| 1. | I | Toluene | B | 100 | 80 | S |
| 2. | I | Toluene | D | 100 | 80 | S |
| 3. | I | 1,4-dioxane | E | 100 | 76 | S |
| 4. | III | 1,4-dioxane | H | 100 | 76 | S |
| 5. | VI | 1,4-dioxane | A | 100 | 76 | S |
| 6. | VI | 1,4-dioxane | H | 100 | 76 | S |

The results in Table 3 substantiate that the process of the present invention provides high conversion efficiency for the hydrogenation of imines, even at substrate to catalyst ratio 3000, such that the process enables 100% conversion of the starting material to the target product having >76% enantiomeric excess of the target product.

Example 5

Hydrogenation of 2-ethyl-N-(1-methoxypropan-2-ylidene)-6-methylaniline using Ligand [(1R,2R,3S)-1,2-dimethyl-2,3-bis(diphenyl phosphinomethyl)cyclopentyl]methanol (I)

The experimental procedure of Example 1 above was followed for ligand (I) of present invention, wherein substrate to catalyst ratio is 10,000. The results for the final product for conversion (%) and ee (%) is tabulated in the accompanying Table 4.

TABLE 4

| Sr. No. | Ligand | Solvent | Additive | Conversion (%) | ee (%) | Abs. conf. |
|---|---|---|---|---|---|---|
| 1. | I | Toluene | E | 100 | 76 | S |

The results in Table 4 substantiate that the process of the present invention provides high conversion efficiency for the hydrogenation of imines, even at substrate to catalyst ratio 10,000, such that the process enables 100% conversion of the starting material to the target product having 76% enantiomeric excess of the target product.

Example 6

Hydrogenation of 2-ethyl-N-(1-methoxypropan-2-ylidene)-6-methylaniline using Rh(COD)$_2$BF$_4$ and (R)-3-di-(3,5-dimethylphenyl)phosphino-2-(4-diphenylphosphino-2,5-dimethylthienyl-3)-1,7,7-trimethylbicyclo-[2,2,1]hept-2-ene (III)

0.67 mg (0.001 mmol) of the ligand (III), 0.41 mg (0.001 mmol) of Rh(COD)$_2$BF$_4$ and 0.24 mg (0.004 mmol) of acetic acid were mixed together under argon in 0.1 ml dichloromethane and the mixture was stirred at room temperature for 20 min). 41 mg (0.200 mmol) of the substrate 2-ethyl-N-(1-methoxypropan-2-ylidene)-6-methylaniline in methylene chloride solvent (0.4 ml of 0.5M solution of substarte in methylene chloride) was then added. The reaction mixtures were subsequently introduced into the autoclave and the autoclave was purged with hydrogen. Then under pressure of 40 bar hydrogen, the reaction was warmed at 40° C. for 18 hr.

After cooling down and release of pressure a sample on analysis showed 99% conversion (GC analysis) with enantiomeric excess (ee) of S isomer of amine at 76% (chiral HPLC).

It has been surprisingly found that using commercially less expensive ligand-catalyst system, in an enantiomeric selective hydrogenation process of the present invention shows a high conversion efficiency for the hydrogenation of imines such that the process enables ≧99% conversion of the starting material to the target product having >76% enantiomeric excess of the target product.

The catalyst system comprising ligands of present invention affords a high conversion of the starting material to the target product having high enantiomeric excess of the target product even without acetic acid or additives and without changing the turn-over-frequency or enantiomeric selectivity the catalyst system.

Example 7

Hydrogenation of 2-ethyl-N-(1-methoxypropan-2-ylidene)-6-methylaniline using Ligand [(1R,2R,3S)-1,2-dimethyl-2,3-bis(diphenylphosphinomethyl)cyclopentyl]methanol (I)

15.10 mg (0.0288 mmol) of ligand [(1R,2R,3S)-1,2-dimethyl-2,3-bis(diphenyl phosphinomethyl)cyclopentyl]methanol, 6 mg (0.0089 mmol) of [Ir(COD)Cl]$_2$ and 60 mg (0.142 mmol) of triphenyl phosphonium dibromide were mixed together under argon in 10 ml toluene and the mixture was stirred at room temperature for 30 min. Meanwhile 25 g (0.122 mol) of 2-ethyl-N-(1-methoxypropan-2-ylidene)-6-methylaniline in 20 ml toluene was introduced to the autoclave. The catalyst solution was then introduced to the autoclave and the autoclave was purged with hydrogen at 80 bar pressure. The reaction mixture was heated to 50° C. temperature. After reaction completion of 18 hr, the mass was cooled to room temperature and pressure was released. A sample on analysis showed complete conversion to amine. The reaction mixture was withdrawn from the autoclave.

The solvent was evaporated and residue was distilled under high vacuum (1-2 torr) to get 24.3 g pale yellow amine with 98% purity and 88% S-isomer (ee 76%).

Example 8

Hydrogenation of 2-ethyl-N-(1-methoxypropan-2-ylidene)-6-methylaniline using Ligand [(1R,2R,3S)-1,2-dimethyl-2,3-bis(diphenyl phosphinomethyl)cyclopentyl]methanol (I)

7.20 mg (0.0137 mmol) of ligand [(1R,2R,3S)-1,2-dimethyl-2,3-bis(diphenyl phosphinomethyl)cyclopentyl]methanol, 2.7 mg (0.0040 mmol) of [Ir(COD)Cl]$_2$ and 31 mg (0.073 mmol) of triphenyl phosphonium dibromide were mixed together under argon in 10 ml toluene and the mixture was stirred at room temperature for 30 min. Meanwhile 35 g (0.171 mol) of 2-ethyl-N-(1-methoxypropan-2-ylidene)-6-methylaniline in 20 ml toluene was introduced to the 100 ml SS316 autoclave. The catalyst solution was then introduced to the autoclave and the autoclave was purged with hydrogen at 80 bar pressure. The reaction mixture was heated to 50° C. temperature. After reaction completion of 18 hr, the mass was cooled to room temperature and pressure was released. A sample on analysis showed complete conversion to amine The reaction mixture was withdrawn from the autoclave. The solvent was evaporated and residue was distilled under high vacuum (1-2 torr) to get 34.1 g pale yellow amine with 99% purity and 89% S-isomer (ee 78%).

Example 9

Hydrogenation of 2-ethyl-N-(1-methoxypropan-2-ylidene)-6-methylaniline using Ligand [(1R,2R,3S)-1,2-dimethyl -2,3-bis(diphenyl phosphinomethyl) cyclopentyl]methanol (I)

The experimental procedure of Example 7 above was followed with following quantities:

5.70 mg (0.0109 mmol) of ligand [(1R,2R,3S)-1,2-dimethyl-2,3-bis(diphenyl phosphinomethyl)cyclopentyl] methanol, 2.1 mg (0.0031 mmol) of [Ir(COD)Cl]$_2$ and 70 mg (0.166 mmol) of triphenyl phosphonium dibromide were mixed together under argon in 10 ml toluene and the mixture was stirred at room temperature for 30 min. Meanwhile 58 g (0.283 mol) of 2-ethyl-N-(1-methoxypropan-2-ylidene)-6-methylaniline in 5 ml toluene was introduced to the 100 ml SS316 autoclave. The reaction was carried out exactly as per example 7. A sample on analysis showed complete conversion to amine. 56 g product was obtained after distillation under high vacuum (1-2 torr) as pale yellow oil in 97% purity and 87% S-isomer (ee 74%).

Example 10

Hydrogenation of 2-ethyl-N-(1-methoxypropan-2-ylidene)-6-methylaniline using ligand [(1R,2R,3S)-1, 2-dimethyl -2,3-bis(diphenyl phosphinomethyl)cyclopentyl]methanol (I)

The experimental procedure of Example 7 above was followed with following quantities:

2.60 mg (0.005 mmol) of ligand [(1R,2R,3S)-1,2-dimethyl-2,3-bis(diphenyl phosphinomethyl)cyclopentyl] methanol, 1.10 mg (0.0016 mmol) of [Ir(COD)Cl]$_2$ and 140 mg (0.332 mmol) of triphenyl phosphonium dibromide were mixed together under argon in 10 ml toluene and the mixture was stirred at room temperature for 30 min. Meanwhile 58 g (0.283 mol) of 2-ethyl-N-(1-methoxypropan-2-ylidene)-6-methylaniline in 5 ml toluene was introduced to the 100 ml SS316 autoclave: The reaction was carried out exactly as per example 7. A sample on analysis showed complete conversion to amine. 57 g product was obtained after distillation under high vacuum (1-2 torr) as pale yellow oil in 98% purity and 88% S-isomer (ee 76%).

Example 11

Hydrogenation of 2-ethyl-N-(1-methoxypropan-2-ylidene)-6-methylaniline using Ligand [(1R,2R,3S)-1,2-dimethyl -2,3-bis(diphenyl phosphinomethyl) cyclopentyl]methanol (I)

9.50 mg (0.0181 mmol) of ligand [(1R,2R,3S)-1,2-dimethyl-2,3-bis(diphenyl phosphinomethyl)cyclopentyl] methanol, 4 mg (0.0059 mmol) of [Ir(COD)Cl]$_2$ and 490 mg (1.161 mmol) of triphenyl phsophonium dibromide were mixed together under argon in 10 ml toluene and the mixture was stirred at room temperature for 30 min. Meanwhile 250 g (1.22 mol) of 2-ethyl-N-(1-methoxypropan-2-ylidene)-6-methylaniline in 20 ml toluene was introduced to 400 ml capacity autoclave. The catalyst solution was then introduced to the autoclave and the autoclave was purged with hydrogen at 80 bar pressure. The reaction mixture was heated to 50° C. temperature. After reaction completion of 18 hr, the mass was cooled to room temperature and pressure was released. The reaction mixture was withdrawn from the autoclave. A sample on analysis showed complete conversion to amine The solvent was evaporated and residue was distilled under high vacuum (1-2 torr) to get 245 g pale yellow amine in 98.5% purity and 89% S-isomer isomer (ee 78%).

Example 12

Hydrogenation of 2-ethyl-N-(1-methoxypropan-2-ylidene)-6-methylaniline using Ligand [(1R,2R,3S)-1,2-dimethyl -2,3-bis(diphenyl phosphinomethyl) cyclopentyl]methanol (I)

7.50 mg (0.0143 mmol) of ligand [(1R,2R,3S)-1,2-dimethyl-2,3-bis(diphenyl phosphinomethyl)cyclopentyl] methanol, 3 mg (0.0044 mmol) of [Ir(COD)Cl]$_2$ and 290 mg (0.6873 mmol) of triphenyl phosphonium dibromide were mixed together under argon in 10 ml toluene and the mixture was stirred at room temperature for 30 min. Meanwhile 280 g (1.366 mol) of 2-ethyl-N-(1-methoxypropan-2-ylidene)-6-methylaniline in 20 ml toluene was introduced to 400 ml capacity autoclave. The catalyst solution was then introduced to the autoclave and the autoclave was purged with hydrogen at 80 bar pressure. The reaction mixture was heated to 50° C. temperature. After reaction completion of 18 hr, the mass was cooled to room temperature and pressure was released. A sample on analysis showed 99% conversion to amine. The material was taken out from autoclave and toluene was distilled off. The crude product was distilled under high vacuum (1-2 torr) to get 275 g pale yellow colour product in 98% purity and 89% S-isomer (ee 78%).

All above reactions were carried out at a defined temperature of 50° C. and defined pressure of 80 bar. Further experiments were carried out exactly with same quantities as in example 7 except the temperature and pressure of reaction. It was surprisingly found that the process of present invention show higher enantiomeric excess, ≧76% particularly at temperature 50° C. and pressure 80 bar.

Example 13

Hydrogenation of 2-ethyl-N-(1-methoxypropan-2-ylidene)-6-methylaniline using Ligand [(1R,2R,3S)-1,2-dimethyl -2,3-bis(diphenyl phosphinomethyl) cyclopentyl]methanol (I)

The reaction was carried out exactly with same quantities as in example 7 except the temperature of reaction. The temperature was 80° C. The reaction was complete in 18 hr, the mass was cooled to room temperature and pressure was released. A sample on analysis showed complete conversion to amine. The solvent was evaporated and residue was distilled under high vacuum (1-2 torr) to get 24.1 g pale yellow amine in 99% purity and 96.5% yield with 85% S-isomer (ee 70%).

Example 14

Hydrogenation of 2-ethyl-N-(1-methoxypropan-2-ylidene)-6-methylaniline using Ligand [(1R,2R,3S)-1,2-dimethyl -2,3-bis(diphenyl phosphinomethyl) cyclopentyl]methanol (I)

The reaction was carried out exactly with same quantities as in example 7 except the temperature of reaction. The temperature here was 40° C. The reaction was complete in 18 hr, the mass was cooled to room temperature and pressure was released. A sample on analysis showed 95% conversion to amine. The solvent was evaporated and residue was distilled under high vacuum (1-2 torr) to get 24.0 g pale yellow amine in 95% purity and 95% yield with 88% S-isomer (ee 76%).

Example 15

Hydrogenation of 2-ethyl-N-(1-methoxypropan-2-ylidene)-6-methylaniline using Ligand [(1R,2R,3S)-1,2-dimethyl -2,3-bis(diphenyl phosphinomethyl) cyclopentyl]methanol (I)

The reaction was carried out exactly with same quantities as in example 7 except the hydrogen pressure during reaction was 100 bars. The reaction was complete in 18 hrs, the mass was cooled to room temperature and pressure was released. A sample on analysis showed complete conversion to amine. The solvent was evaporated and residue was distilled under high vacuum (1-2 torr) to get 24.1 g pale yellow amine in 98% purity and 96.6% yield with 87% S-isomer (ee 74%).

It has been surprisingly found that using commercially less expensive ligand-catalyst system, in an enantiomeric selective hydrogenation process of the present invention shows a high conversion efficiency for the hydrogenation of imines such that the process enables >99% conversion of the starting material to the target product having ≧76% enantiomeric excess of the target product at an elevated hydrogen pressure.

The catalyst system comprising ligands of present invention gives high conversion of the starting material to the target product having high enantiomeric excess of the target product even without acetic acid and without affecting productivity and activity of the catalyst system. It has further been found that ligand I provides a superior turn-over-number at desirable conversion percentage and enantioselectivity, as shown in table 5 appearing hereinafter, which is not intended to limit the scope of the invention in any manner:

TABLE 5

| S No. | Parameter | Experimental conditions | | | | | | | |
|---|---|---|---|---|---|---|---|---|---|
| | | 1 | 2 | 3 | 4 | 5 | 6 | 7 | 8 |
| 1 | Temperature (° C.) | 50 | 80 | 40 | 50 | 50 | 50 | 50 | 50 |
| 2 | Pressure (bar) | 80 | 80 | 80 | 100 | 80 | 80 | 80 | 80 |
| 3 | Ligand | I | I | I | I | Xyliphos | I | I | I |
| 4 | Metal | Ir | Ir | Ir | Ir | Ir | Rh | Ir | Ir |
| 5 | Solvent | Toluene | Toluene | Toluene | Toluene | Toluene | Toluene | CH$_2$Cl$_2$ | Toluene |
| 6 | Additive | E | E | E | E | E | E | E | J |
| 7 | Yield | 96.3 | 96.5 | 95 | 96.6 | 98 | 98 | 69 | 16 |
| 8 | Purity | 98 | 99 | 95 | 98 | 99 | 98 | 70.4 | 17 |
| 9 | EE | 76 | 70 | 76 | 74 | 66 | a) | 60 | b) |
| 10 | TON | 478854 | 19264 | 19264 | 19264 | 200 | 200 | 44456 | 75681 | a) R-isomer of amine is obtained instead of S-isomer
b) The conversion to amine was only 16% in this case.

The invention claimed is:
1. A process for asymmetric hydrogenation of an imine having formula 1:

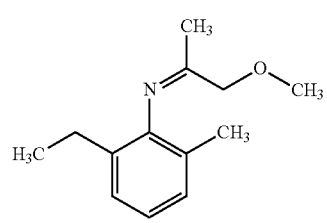

to obtain an amine having formula 2:

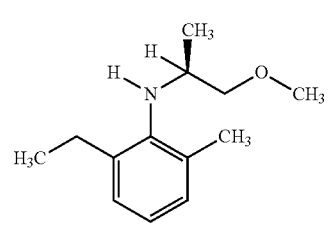

said process comprising contacting said imine having the above formula 1 with hydrogen under elevated pressure in a predetermined organic solvent in the presence of a catalyst system;

said catalyst system comprising a ligand complexed to a metal selected from iridium and rhodium or a salt thereof;

wherein said ligand is at least one selected from the group consisting of a. [(1R,2R,3S)-1,2-dimethyl-2,3-bis(diphenylphosphinomethyl)-cyclopentyl]methanol;

b. (1S,4S, 11R)-1,11-bis-[(diphenylphosphanyl)-methyl]-11-methyl-1,2,3,4-tetrahydro-1,4-methanophenazin;

c. (R)-3-di-(3,5-dimethylphenyl)phosphino-2-(4-diphenylphosphino-2,5-dimethylthienyl-3)-1,7,7-trimethylbicyclo-[2.2.1]-hept-2-ene;

d. (S)-2-[(o-diphenylphosphino)-phenyl]-1-diphenylphosphino-ferrocene;

e. (S)-1-(diphenylphosphino)-2-(S)-(o-diphenylphosphino-α-methoxybenzyl)ferrocene;

f. (+)-(S)-N,N-Dimethyl-1-[(R)-1',2-bis-(Diphenylphosphino)-ferrocenyl]-ethylamine; and g. [(S)-1-[(R)-2-diphenylphosphino)ferrocenyl]-ethyl-di(cyclohexyl)-phosphine.

2. A process for the preparation of a compound of formula 3

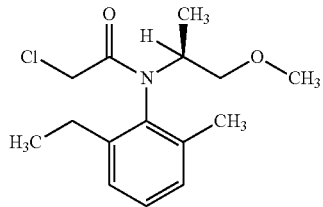

comprising:
(i) asymmetrically hydrogenating an imine having formula 1:

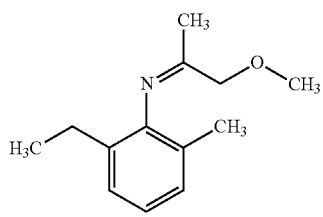

to obtain an amine having formula 2:

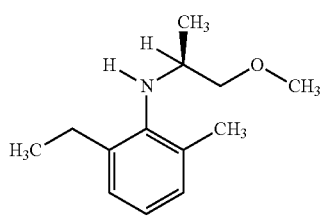

by contacting said imine having the above formula 1 with hydrogen under elevated pressure in a predetermined organic solvent in the presence of a catalyst system;
wherein said catalyst system comprising a ligand complexed to a metal selected from iridium and rhodium or a salt thereof;
wherein said ligand is at least one selected from the group consisting of
a. [(1R,2R,3S)-1,2-dimethyl-2,3-bis(diphenylphosphinomethyl)-cyclopentyl]methanol;
b. (1S,4S,11R)-1,11-bis-[(diphenylphosphanyl)-methyl]-11-methyl-1,2,3,4-tetrahydro-1,4-methano-phenazin;
c. (R)-3-Di-(3,5-dimethylphenyl)phosphino-2-(4-diphenylphosphino-2,5-dimethylthienyl-3)-1,7,7-trimethylbicyclo-[2.2.1]-hept-2-ene;
d. (S)-2-[(o-diphenylphosphino)-phenyl]-1-diphenylphosphino-ferrocene;
e. (S)-1-(diphenylphosphino)-2-(S)-(o-diphenylphosphino-α-methoxybenzyl)ferrocene;
f. (+)-(S)-N,N-Dimethyl-1-[(R)-1',2-bis-(Diphenylphosphino)-ferrocenyl]-ethylamine; and
g. [(S)-1-[(R)-2-diphenylphosphino)ferrocenyl]-ethyl-di(cyclohexyl)-phosphine; and
(ii) reacting said amine having formula 2 with chloroacetyl chloride in the presence of a base in a non-polar solvent at a predetermined temperature.

3. A process for the preparation of a compound of formula 3

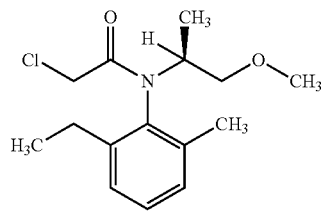

comprising:
(i) reacting a compound of the formula 4:

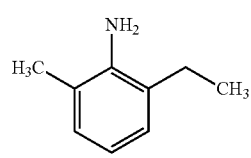

with methoxyacetone having the formula $CH_3OCH_2C(O)CH_3$ to obtain an imine compound of formula 1;
(ii) asymmetrically hydrogenating said imine having formula 1:

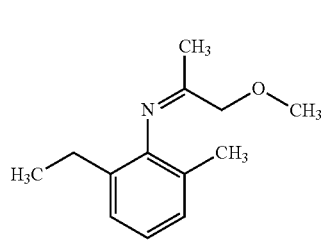

to obtain an amine having formula 2:

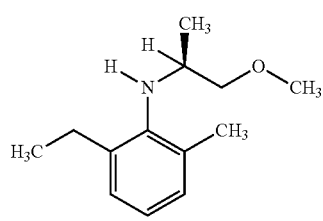

by contacting said imine having the above formula 1 with hydrogen under elevated pressure in a predetermined organic solvent in the presence of a catalyst system;
wherein said catalyst system comprising a ligand complexed to a metal selected from iridium and rhodium or a salt thereof;
wherein said ligand is selected from the group consisting of
a. [(1R,2R,3S)-1,2-dimethyl-2,3-bis(diphenylphosphinomethyl)-cyclopentyl]methanol;
b. (1S,4S,11R)-1,11-bis-[(diphenylphosphanyl)-methyl]-11-methyl-1,2,3,4-tetrahydro-1,4-methano-phenazin;

c. (R)-3-di-(3,5-dimethylphenyl)phosphino-2-(4-diphenylphosphino-2,5-dimethylthienyl-3)-1,7,7-trimethylbicyclo-[2.2.1]-hept-2-ene;

d. (S)-2-[(o-diphenylphosphino)-phenyl]-1-diphenylphosphino-ferrocene;

e. (S)-1-(Diphenylphosphino)-2-(S)-(o-diphenylphosphino-α-methoxybenzyl)ferrocene;

f. (+)-(S)-N,N-Dimethyl-1-[(R)-1',2-bis-(Diphenylphosphino)-ferrocenyl]-ethylamine; and g. [(S)-1-[(R)-2-diphenylphosphino) ferrocenyl]-ethyl-di(cyclohexyl)-phosphine; and (iii) reacting said amine having formula 2 with chloroacetyl chloride in the presence of a base in a non-polar solvent at a predetermined temperature.

4. A process as claimed in claim 1, wherein said step of contacting said imine with hydrogen under elevated pressure is carried out in the presence of an additive.

5. The process as claimed in claim 4, wherein said additive is selected from the group comprising diadamantyl butyl phosphonium hydroiodide (A), diadamantyl benzyl phosphonium hydrobromide (B), triphenyl phosphonium diiodide (C), isopropyl triphenylphosphonium iodide (D), triphenyl phosphonium dibromide (E), methyl triphenyl phosphonium bromide (F), tetrabutyl ammonium iodide(G), copper(II) triflate(H) and yetribium(II) triflate(I), triphenylphosphonium dichloride (J).

6. A process as claimed in claim 1, wherein said step of contacting said imine with hydrogen is carried out in an inert organic solvent selected from the group comprising toluene, 1,4-dioxane, methanol, tetrahydrofuran, dichloromethane and the like.

7. A process as claimed in claim 1, wherein the molar ratio of said imine to said catalyst system is from about 200 to about 500000.

8. A process as claimed in claim 1, wherein said step of contacting said imine with hydrogen is carried out at a temperature of from about 10° C. to 100° C.

9. A process as claimed in claim 1, wherein said amine of formula 2 is reacted with chloroacetyl chloride at a temperature of from about 0° C. to about 5° C.

10. A process as claimed in claim 1, wherein said step of contacting said imine with hydrogen is carried out at an elevated hydrogen pressure of from about 5 bar to about 150 bar.

11. A process for asymmetric hydrogenation of an imine having formula 1:

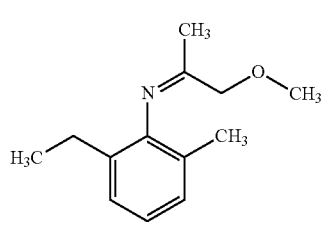

to obtain an amine having formula 2:

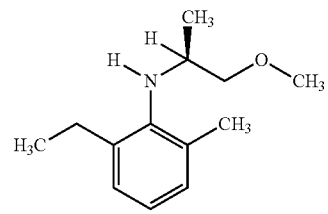

said process comprising contacting said imine having the above formula 1 with hydrogen under an elevated pressure of about 80 bar at a temperature of about 50° C. in toluene in the presence of a catalyst system comprising a ligand having a formula [(1R,2R,3S)-1,2-dimethyl-2,3-bis (diphenylphosphinomethyl)-cyclopentyl] methanol complexed to iridium metal or a salt thereof.

12. A process for the preparation of a compound of formula 3

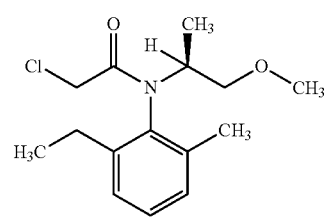

comprising:

(i) asymmetrically hydrogenating an imine having formula 1:

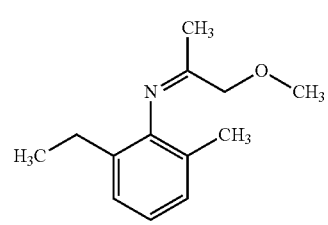

to obtain an amine having formula 2:

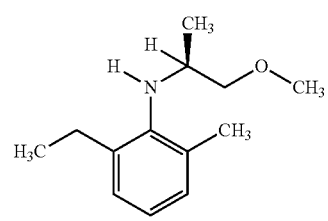

by contacting said imine having the above formula 1 with hydrogen under an elevated pressure of about 80 bar at a temperature of about 50° C. in toluene in the presence of a catalyst system comprising a ligand having a formula [(1R, 2R,3S)-1,2-dimethyl-2,3-bis (diphenylphosphinomethyl)-cyclopentyl] methanol complexed to iridium metal or a salt thereof; and (ii) reacting said amine having formula 2 with chloroacetyl chloride in the presence of a base in a non-polar solvent at a predetermined temperature.

13. A process for the preparation of a compound of formula 3

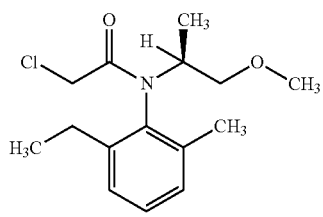

3 comprising:
(i) reacting a compound of the formula 4:

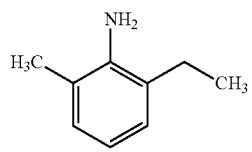

4 with methoxyacetone having the formula $CH_3OCH_2C(O)CH_3$ to obtain an imine compound of formula 1;
(ii) asymmetrically hydrogenating an imine having formula 1:

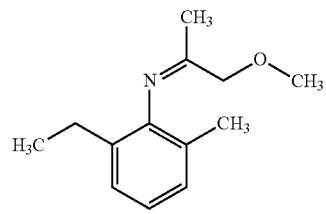

1 to obtain an amine having formula 2:

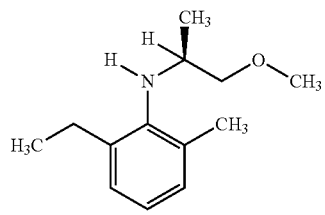

2 by contacting said imine having the above formula 1 with hydrogen under an elevated pressure of about 80 bar at a temperature of about 50° C. in toluene in the presence of a catalyst system comprising a ligand having a formula [(1R, 2R,3S)-1,2-dimethyl-2,3-bis(diphenylphosphinemethyl)-cyclopentyl]methanol complexed to iridium metal or a salt thereof; and (iii) reacting said amine having formula 2 with chloroacetyl chloride in the presence of a base in a non-polar solvent at a predetermined temperature.

14. A process as claimed in claim 11, wherein said step of contacting an imine having said formula 1 with hydrogen is carried out in the presence of an additive.

15. A process as claimed in claim 14, wherein said additive is triphenyl phosphonium dibromide.

16. A process as claimed in claim 11, wherein the substrate-to-catalyst ratio of said imine compound of formula 1 to said catalyst system is up to about 500000.

17. The process of claim 1, wherein the process is conducted in the absence of an acid.

18. The process of claim 2, wherein the process is conducted in the absence of an acid.

19. The process of claim 3, wherein the process is conducted in the absence of an acid.

* * * * *

UNITED STATES PATENT AND TRADEMARK OFFICE
CERTIFICATE OF CORRECTION

PATENT NO. : 8,461,386 B2
APPLICATION NO. : 12/935166
DATED : June 11, 2013
INVENTOR(S) : Shroff et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 299 days.

Signed and Sealed this
Eighth Day of September, 2015

Michelle K. Lee
*Director of the United States Patent and Trademark Office*